United States Patent [19]

Demarest et al.

[11] Patent Number: 5,568,593
[45] Date of Patent: Oct. 22, 1996

[54] ROBOTIC CONTROL SYSTEM FOR A NEEDLE SORTING AND FEEDING APPARATUS

[75] Inventors: David Demarest, Parsippany, N.J.; Dennis P. Yost, Wayne, Pa.

[73] Assignee: Ethicon, Inc., Somerville, N.J.

[21] Appl. No.: 181,624

[22] Filed: Jan. 13, 1994

[51] Int. Cl.⁶ .............. B05B 19/04; G25J 11/00; G25J 9/00
[52] U.S. Cl. .............. 395/82; 395/80; 395/94; 901/7; 901/9
[58] Field of Search .............. 395/80, 82, 94; 901/7, 9

[56] References Cited

U.S. PATENT DOCUMENTS

| | | | |
|---|---|---|---|
| 3,611,551 | 10/1971 | Shave et al. | 29/515 |
| 3,980,177 | 9/1976 | McGregor | 206/63.3 |
| 4,187,051 | 2/1980 | Kirsch et al. | 414/744 |
| 4,437,114 | 3/1984 | LaRussa | 358/101 |
| 4,674,869 | 6/1987 | Pryor et al. | 356/1 |
| 4,835,450 | 5/1989 | Suzuki | 318/568.13 |
| 4,922,904 | 5/1990 | Uetake et al. | 606/226 |
| 5,195,234 | 3/1993 | Pine et al. | 29/720 |
| 5,343,283 | 8/1994 | Van Dorsselaer et al. | 358/445 |

Primary Examiner—Robert W. Downs
Assistant Examiner—A. Katbab

[57] ABSTRACT

A control system for a needle infeed device for automatically transferring needles randomly positioned on an indexing conveyor to an engagement device for subsequent conveyance to a processing location. The needle infeed device comprises one or more robots each having a gripper means for picking and placing the needles in the engagement device. The control system comprises a control device for pausing the indexing conveyor to create a dwell cycle for the infeed device, vision tracking apparatus in communication with the control device for imaging needles at one or more predetermined locations on the indexing conveyor and for determining positional and orientation data for each recognized needle during the dwell cycle, a memory device for temporarily storing the positional and orientation data received from the vision tracking device, and, a robot control device for accessing the stored positional and orientation data corresponding to the imaged needles from the memory means and for enabling one of the robots to pick up the imaged needle in accordance with its respective positional and orientation data in order to place the needle in the engagement device.

23 Claims, 14 Drawing Sheets

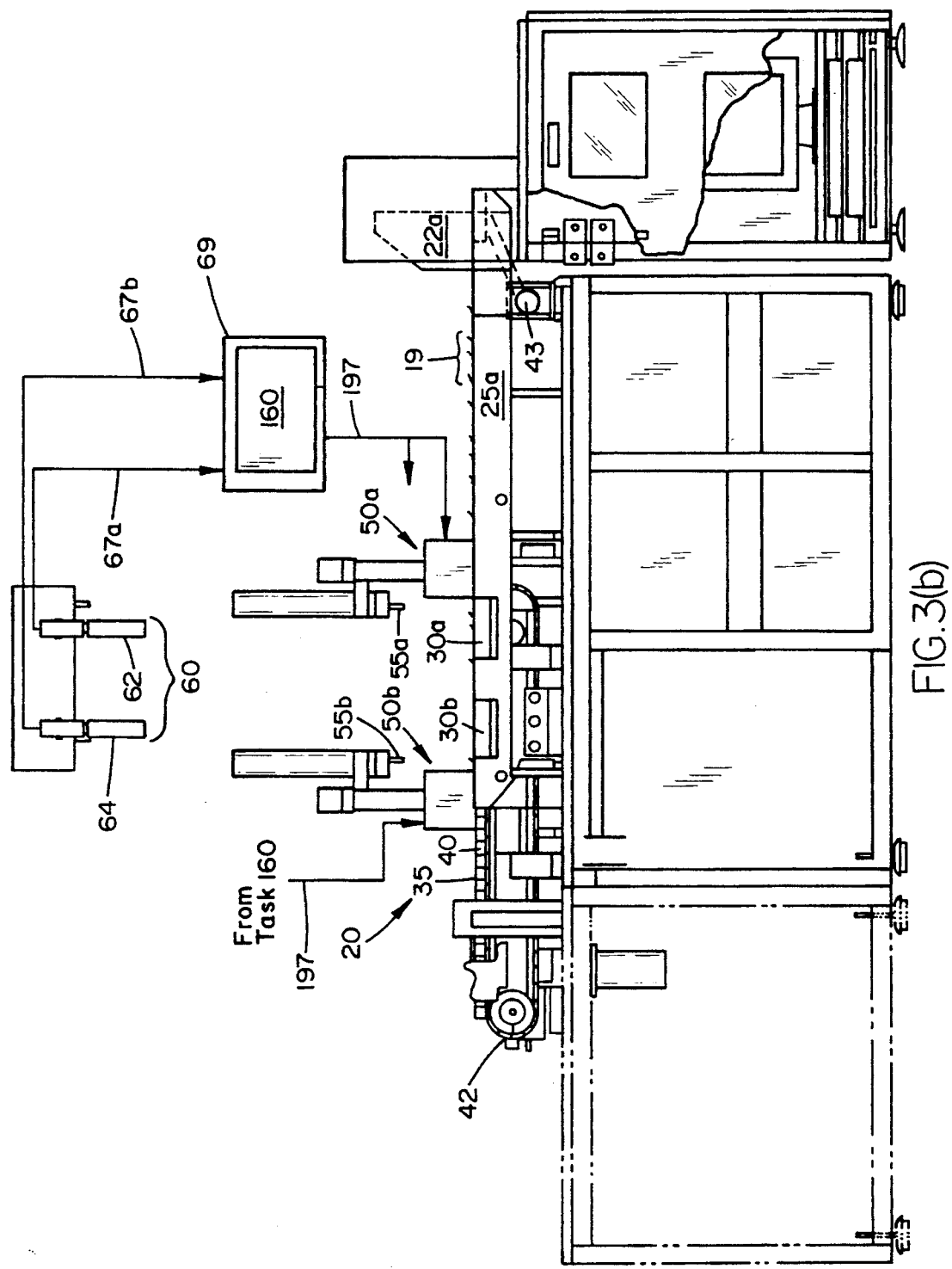

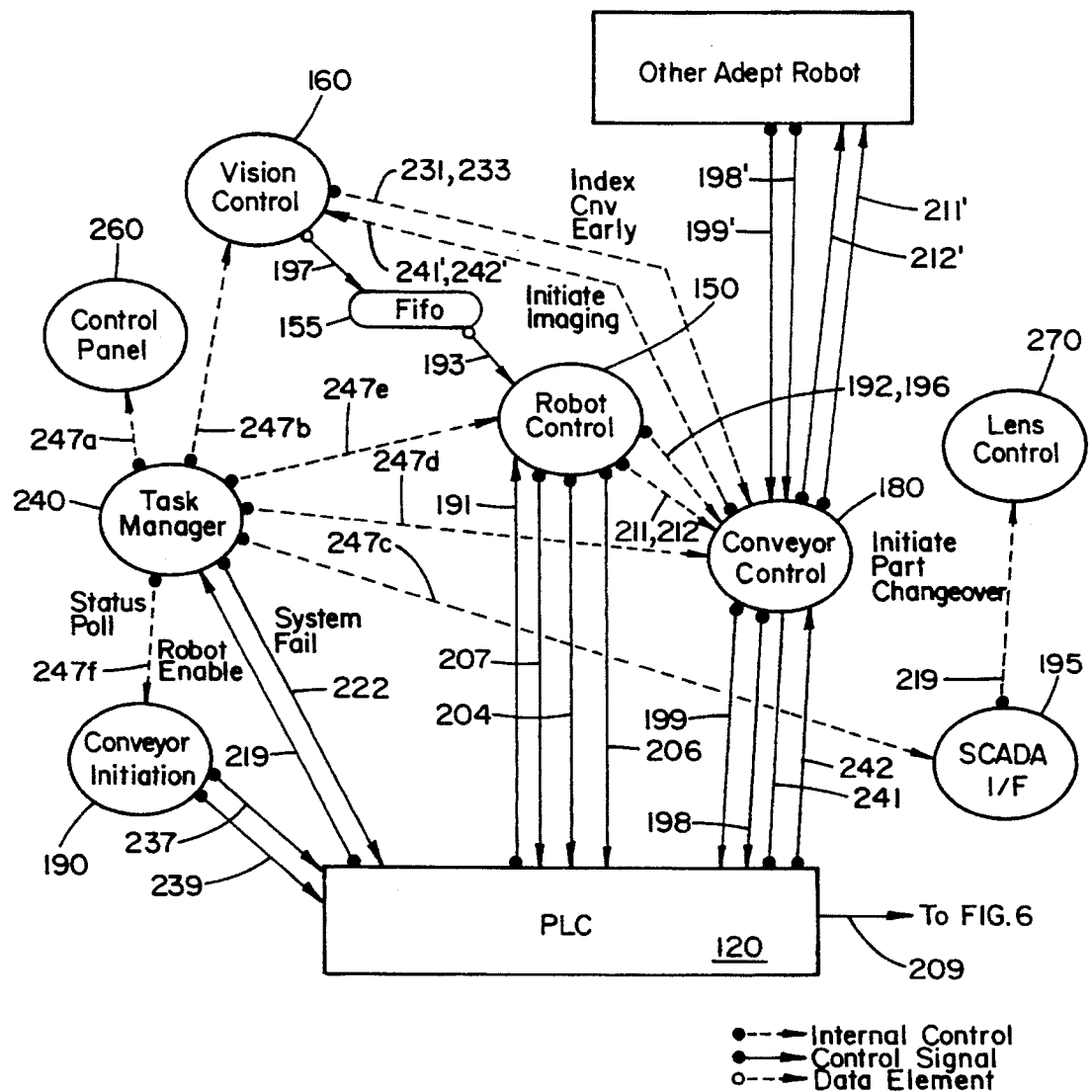
FIG.7 : Needle Infeed System Task Diagram

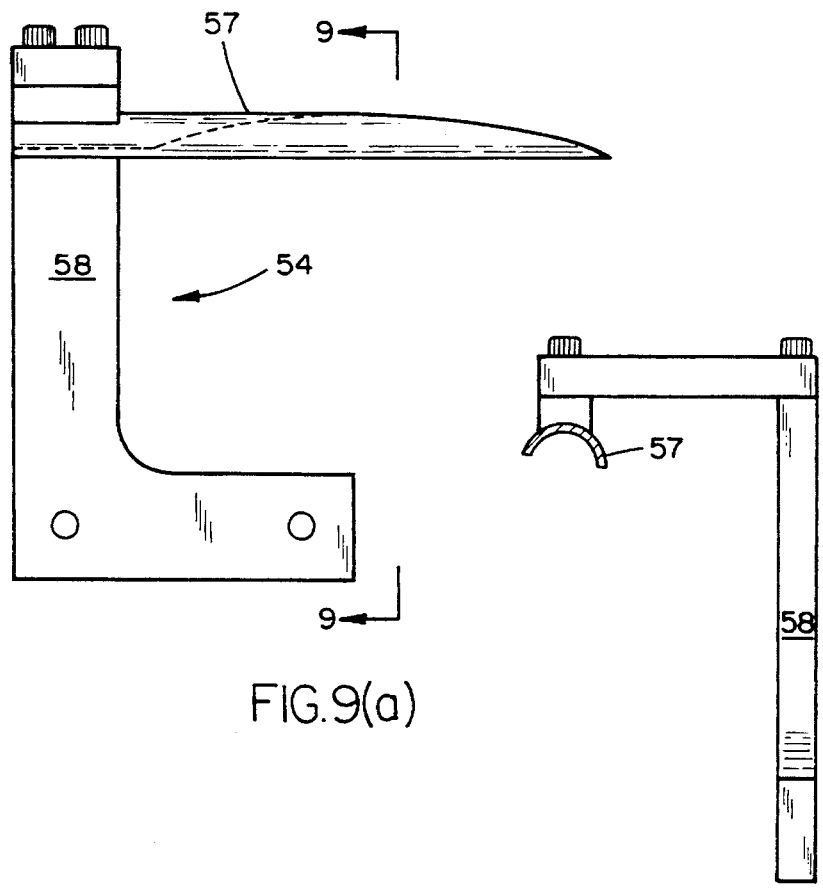
FIG.9(a)
FIG.9(b)
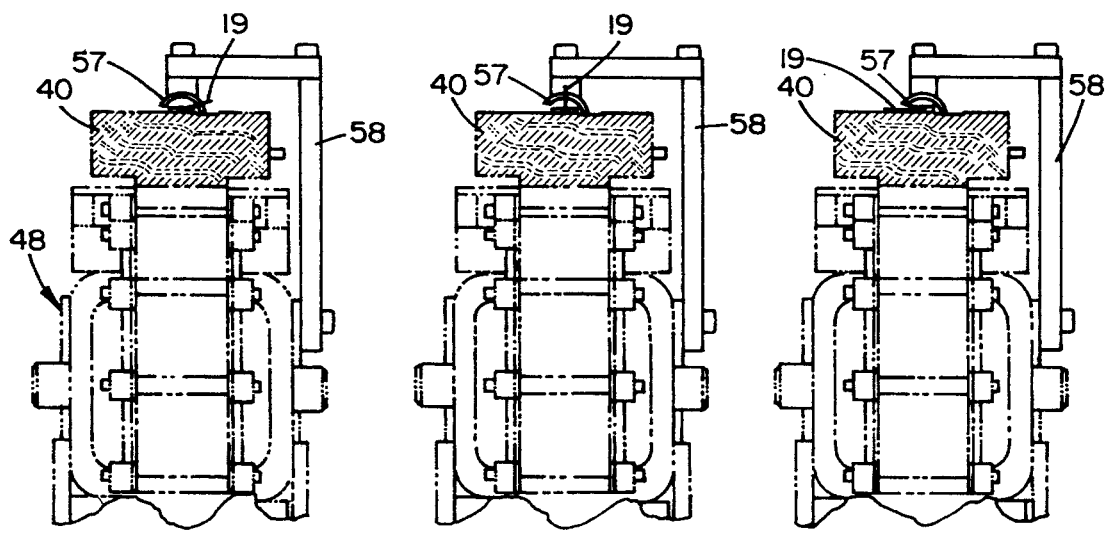
FIG.9(c)   FIG.9(d)   FIG.9(e)

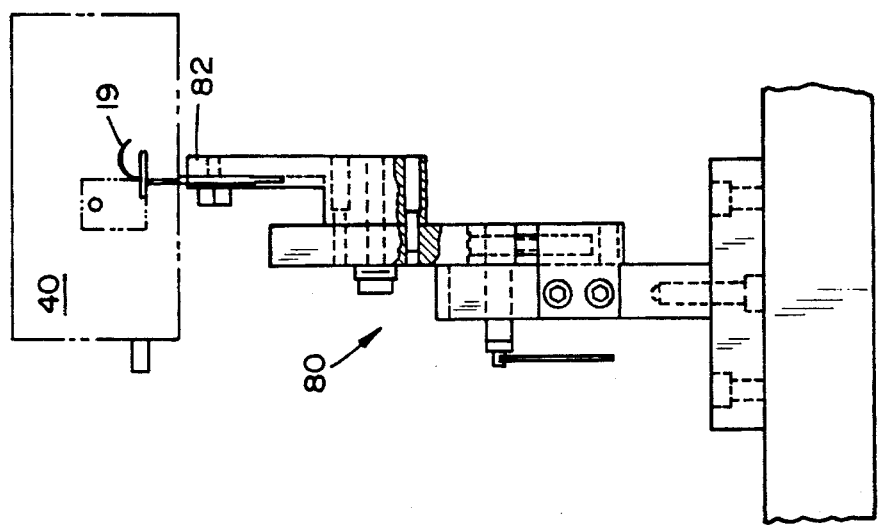
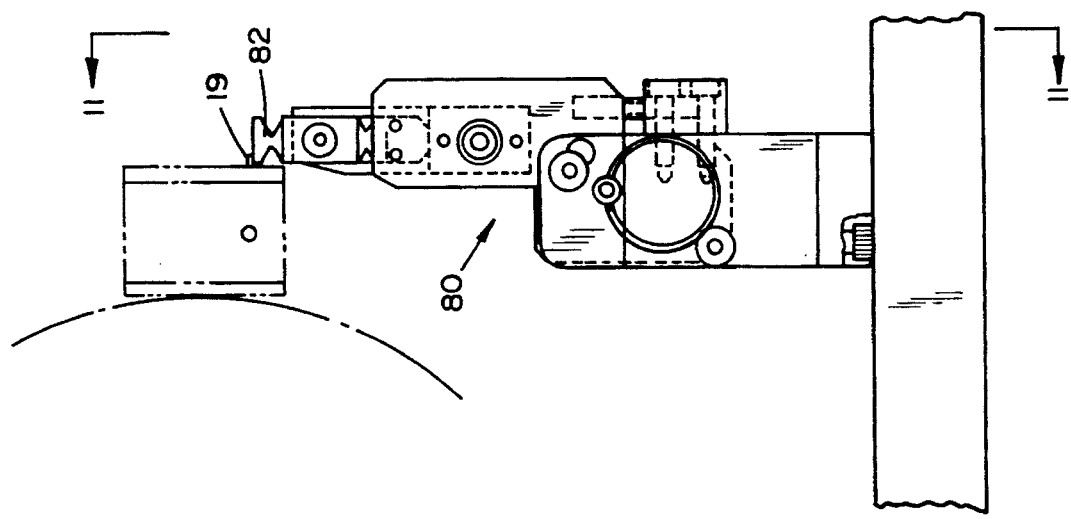

ROBOTIC CONTROL SYSTEM FOR A NEEDLE SORTING AND FEEDING APPARATUS

FIELD OF THE INVENTION

The present invention relates generally to machines for automatically producing armed surgical needles, such as surgeons' needles having sutures attached thereto, and more specifically, to a control system for a needle infeed apparatus that automatically transfers randomly positioned surgical needles at one location and conveys them to another location in an oriented position.

DESCRIPTION OF THE PRIOR ART

Most armed surgical needles, i.e., needles having sutures attached to one end thereof, that are in present use by surgeons and medical personnel, are manufactured utilizing manual and semi-automated procedures such as those described in U.S. Pat. Nos. 3,611,551, 3,980,177, and 4,922,904. For instance, as described in U.S. Pat. No. 3,611,551, manual intervention is required by an operator to accurately position a suture within the needle for swaging and to adjust swaging dies to increase or decrease swage pressure when suture strands of different gauges are to be swaged. This process is costly in terms of man-hour labor and efficiency because manual positioning is required for swaging to take place.

Presently, suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to prepare the rack for the cutting of the suture material wound thereabout. Moreover, manual intervention is required to change the rack each time a suture strand of different length is desired.

In U.S. Pat. No. 4,922,904, the suture material is supplied wound on a bobbin and is fed through various guide means and a heater for straightening the material, prior to insertion within the crimping cavity of the surgical needle. In one embodiment shown therein, an elaborate television monitoring means is required for aligning the drawn suture within the crimping cavity of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is fed a predetermined distance prior to cutting to obtain a suture strand of predetermined length. Thus, to obtain uniform lengths of suture material every time requires careful manipulations and precise controls, and the processes used to accomplish these tasks are also costly in terms of man-hour labor and efficiency.

It would be highly desirable to provide an armed needle production and packaging system that is fully automated and that can automatically feed surgical needles for conveyance to an automatic swaging machine for the swaging of sutures thereto.

It would also be highly desirable to provide a needle sorting device that can efficiently and accurately orient a needle for subsequent transference to an automatic swaging station.

Even more desirable would be a provision of a robotic control system to maintain the efficiency and integrity of the needle sorting and conveying function.

SUMMARY OF THE INVENTION

Accordingly, it is an object of the instant invention to provide a control system for an automatic needle sorting device that conveys properly oriented individual needles to a fully automated needle swaging station.

It is another object of the instant invention to provide a cost effective needle sorting device that virtually eliminates operator exposure to repetitive manual operations.

Furthermore, it is an object of the instant invention to provide a robotic control system for an automatic needle sorting device that maintains the integrity of the needle sorting function, and ensures high-speed and efficient conveyance of sorted, oriented needles to a fully automated needle swaging station.

These and other objects of the present invention are attained with a control system for a needle infeed apparatus for automatically transferring needles randomly positioned on a forwardly indexing conveyor to an engagement device for subsequent conveyance to an automatic needle swaging station. The needle infeed apparatus comprises one or more robots each having a gripper device for picking and placing the needles. The control system comprises: a control device for pausing the indexing conveyor to create a dwell cycle for the infeed device; a vision tracking device for visually recognizing needles at one or more predetermined locations on the indexing conveyor and for determining positional and orientation data for each recognized needle during the dwell cycle; memory device for temporarily storing said positional and orientation data received from the vision tracking device; and, a robot control apparatus for accessing the stored positional and orientation data corresponding to the visually recognized needles from the memory device, and enabling one of the robots to pick up the recognized needle in accordance with its respective positional and orientation data and place the needle in the engagement device.

The needle sorting system is provided with a redundant vision tracking device a second robot assembly means that operate in the manner as described above. The redundancy is designed in the system is to ensure that a continuous and uninterrupted flow of 60 needles/minute is supplied to the automatic swaging station.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 3(*b*) is a side elevational view of the needle sorting device of FIG. 3(*a*) showing the robot assembly above the first and second conveyor means and the tracking means comprising two video cameras for tracking the position of individual needles and the control system means for processing said data.

FIG. 7 is schematic representation of the control and data flow for each of the control tasks of the infeed control system of the present invention.

FIG. 9(a) is a side view of the needle rollover (plow) which ensures uniform orientation of the needle on the conveyor boat prior to automatic swaging.

FIG. 9(b) is a front view of the plow taken along line 9—9 of FIG. 9(a).

FIGS. 9(c)–9(e) is a front view illustrating the plow 54 orienting a needle in one direction upon a boat 40 of the precision conveyor.

FIG. 11(a) is a side view of the stop assembly 80 for further orienting the needle 19 upon conveyor boat 40.

FIG. 11(b) is a front view of the stop assembly 80 for further orienting the needle 19 upon conveyor boat 40 taken along line 11—11 of FIG. 11(a).

DETAILED DESCRIPTION OF THE PREFERRED EMBODIMENT

Figure 2:
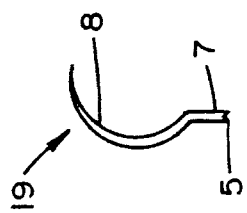
FIG. 2 is a surgical needle 19 with crimping end 85 and barrel portion 83.

This invention is drawn to a control system for a needle infeed apparatus that is designed to automatically sort, singulate, and convey surgical needles of various sizes to an automatic swaging station where sutures are attached to individual needles. A typical surgical needle 19 having a barrel portion 7, an arcuate blade portion 8, and a suture receiving end or opening 5 for swaging a suture thereto, is illustrated in FIG. 2.

Figure 1:
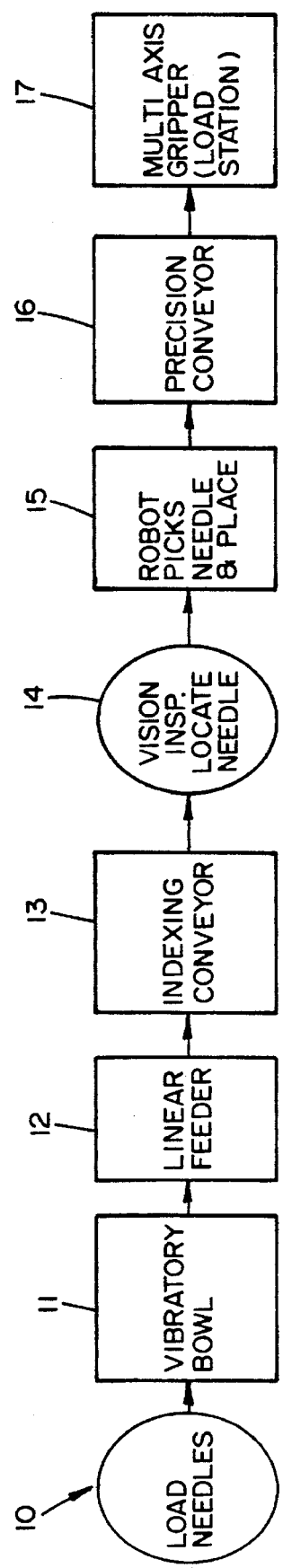
FIG. 1 is a block diagram showing the process flow for the needle sorting apparatus of the present invention.

Generally, in the needle sorting process 10 shown in FIG. 1, needles are first loaded into a vibratory bowl at step 11, automatically sorted and linearly fed at step 12 to a translucent indexing conveyor at step 13, evaluated with respect to orientation and position by a vision tracking system at step 14, picked up by a robot apparatus at step 15, transferred to a engagement boat of a precision conveyor by the robot apparatus at step 16, and finally conveyed to a multi-axis indexing means for further conveyance to subsequent swaging workstation at step 17. An explanation of the apparatus used to carry out each step will be explained in detail hereinbelow. A full detailed description of the needle sorting apparatus can be found in copending patent application U.S. Ser. No. 181,600 entitled NEEDLE SORTING ASSEMBLY, filed Jan. 13, 1994, assigned to the same assignee of the present invention.

Figure 3A:
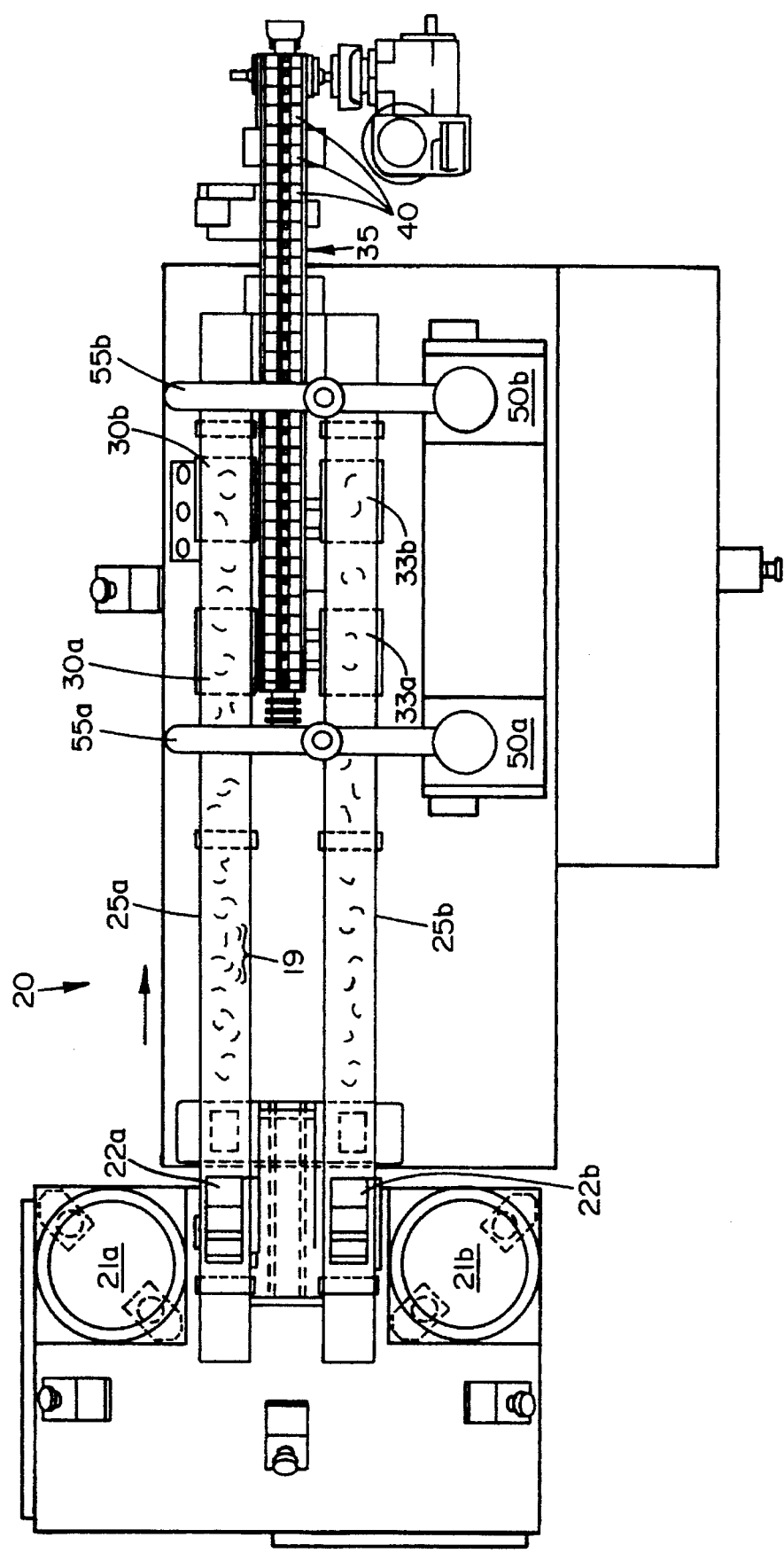
FIG. 3(*a*) is a top view of the needle sorting device 20 of the instant invention.

The preferred embodiment of the needle sorting and infeed apparatus 20 is illustrated in the top view of the system in FIG. 3(a) and the side view of FIG 3(b). As shown therein, needles 19 are delivered in bulk to each of two vibratory bowls or hoppers 21a,b where they are singulated by respective singulating assemblies 22a,b and randomly deposited upon each of two translucent conveyors 25a,b. The two translucent conveyors 25a,b carry the randomly deposited needles 19 in the direction indicated by the arrow in FIG. 3(a) where their position and orientation are evaluated by a remotely located vision tracking system that will be discussed in detail below with respect to FIG. 3(b). This tracking system, evaluates the position and orientation of each available needle upon translucent conveyor 25a as it forwardly conveys the needles over illuminated (backlit) platforms 30a and 30b, and further evaluates the position and orientation of the each available needle upon translucent conveyor 25b as it forwardly conveys the needles over illuminated (backlit) platforms 33a and 33b. The orientation and positional information obtained from the vision tracking system is processed and converted to information usable by each of two robot assemblies 50a,b for instructing respective robot grippers 55a,b to pick up and transfer identified needles from one of the translucent conveyors to individual engagement boats 40, located on a precision conveyor 35 that is also being indexed in the same direction as the translucent conveyors as shown in FIG. 3(a). The control system of the invention instructs a robot gripper, for e.g., gripper 55a of the robot assembly 50a, to grab the tracked needle from one of the two conveyors 25a,b for a dwell cycle of the system, i.e. when the conveyor has paused. If the randomly deposited needles 19 are oriented such that either of the robot grippers 55a,b is unable to pick one of them up or place the needle onto the precision conveyor because of its limited range of motion, the control system will execute a recovery procedure to ensure that there are no shortages of needles 19 to be fed by the precision conveyor 35 to the automatic high-speed swaging workstation (not shown) which can achieve up to 60 needle swages per minute.

In the preferred embodiment, the timing of each conveyor 25a,b is identical, but the dwell periods are out of phase. Because of the phased timing, the vision tracking system will be identifying needles on one indexing conveyor, for e.g. 25a, while both robots are picking needles from the other indexing conveyor 25b and placing each needle in an individual engagement boat of the precision conveyor. Similarly, while both robots are picking needles from the indexing conveyor 25a, the vision tracking system will be identifying needles on the other indexing conveyor 25b.

Figure 4:
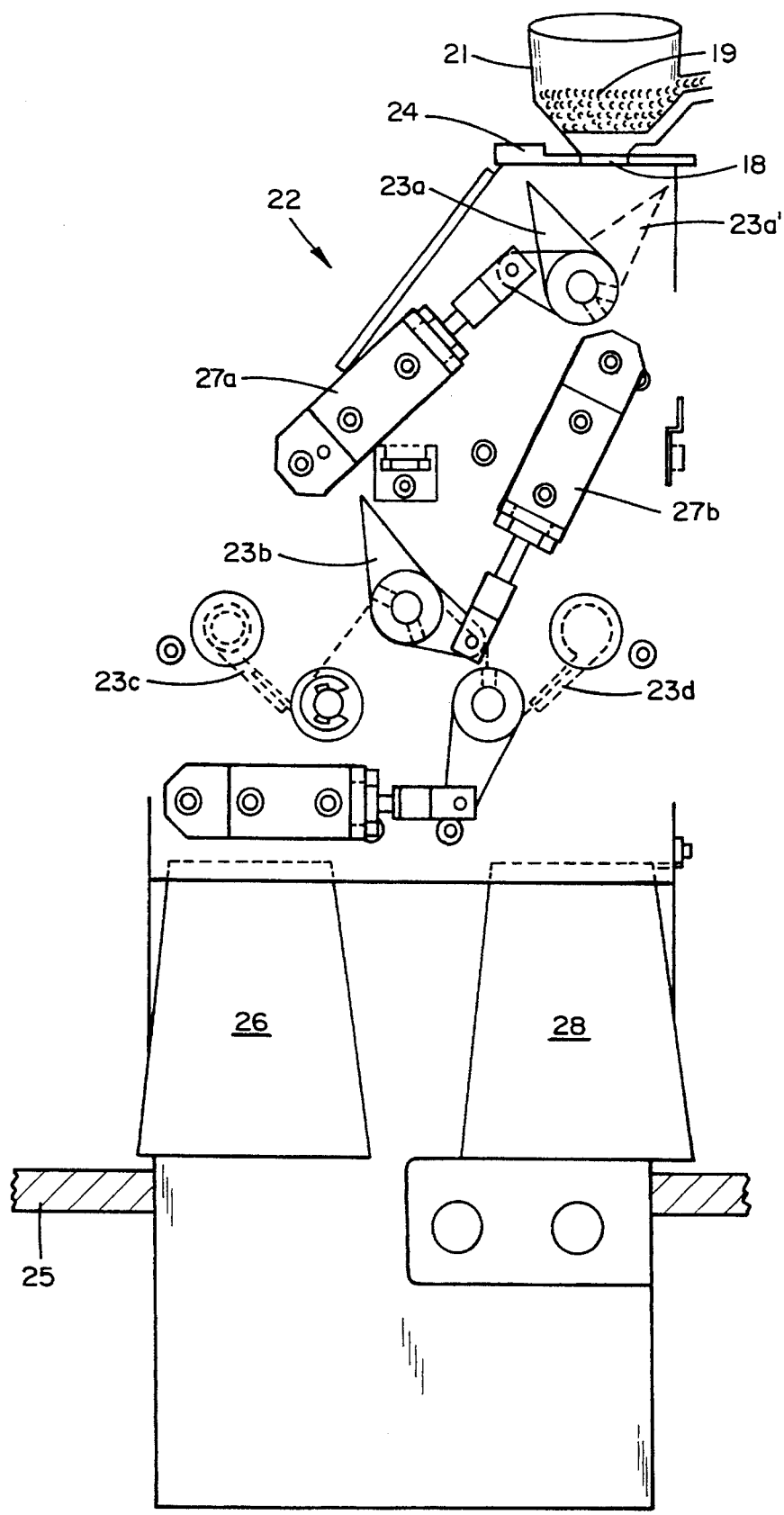
FIG. 4 is a detailed side view of the needle infeed means for singulating and depositing needles onto a translucent conveyor.

The first step of the automatic swage/wind process 10 involves introducing a predetermined amount of needles 19 from an infeed device, such as a bowl or hopper, into a needle singulating assembly. In the preferred embodiment shown in the side view of FIG. 4, a vibratory hopper or bowl 21 is provided with a suitable optical or mechanical counting device such as sensor plate 24 so that up to six (6) needles may be periodically fed into the sorting assembly 22 at any one time. The needles 19 are dispensed from the vibratory hopper 21 through a gate 18, and fall by gravity through a needle singulating assembly 22 which comprises a series of diverter doors 23a,b and trap doors 23c,d that alternate between two positions to allow one half of the needles discharged to drop onto each of two spaced-apart chutes 26,28 and finally onto the moving translucent indexing conveyors 25a,b. With the diverter door 23a in the position shown in FIG. 4, any needle 19 introduced into the needle singulating assembly 22 will be deflected and fall into an external receptacle (not shown) where the needles may be subsequently returned to the hopper 21. When diverter door 22a is in a second position indicated by the dotted line diverter 23a' in FIG. 4, up to twelve (12) needles 9 will be counted by sensor 44 as they fall through the sorting assembly so that they may be singulated by appropriate switching of diverter door 23b and trap doors 23c,d. The reciprocating motion of the diverter doors 23a,b and trap doors 23c,d are timed to ensure that approximately six (6) needles are deposited in two lines of three on each conveyor 25a,b at a time. In the preferred embodiment, this number of needles, as deposited, will occupy approximately eight (8) inches of indexing conveyor length, and thus, ensure that the needles are adequately spaced apart when deposited. Preferably, the diverter doors 23a,b reciprocate under the control of an automatic control system and timed to alternate between two positions to allow approximately three (3) needles at a time to drop onto each translucent indexing conveyor 25a,b via respective discharge chutes 26,28. Both diverter doors 23a,b are respectively driven by cylindrical pistons 27a,b and suitable solenoid or pneumatic motors (not shown). It should be understood that any needle 19 deposited on translucent indexing conveyors 25a,b will be randomly positioned and unoriented. Preferably, each translucent indexing conveyor 25a,b is an endless belt conveyor that is driven at a rate of four inches per second at steady state (4 in./sec) and runs parallel to the precision conveyor 35 as shown in FIGS. 3(a).

As described above, and in view of FIG. 3(a), the robot assembly comprises two robots 50a,b located downstream from each needle singulating assembly 22a,b and proximate both the precision and translucent indexing conveyors. In the preferred embodiment described herein, each robot assembly 50a,b is an Adept® 604-S robot capable of accomplishing needle transfers at a rate of approximately 40 transfers per minute as controlled by each robot's corresponding Adept® CC controller. Each robot is a four-axis SCARA (Selective Compliance Assembly Robot Arm) robot comprising four Joints: Joint 1, being the shoulder joint having a rotational range of motion of +/−100°; Joint 2, the elbow joint, having a rotational range of motion of +/−140°; Joint 3 providing translational motion for a robot quill for up to 150 mm in an up down motion; and, Joint 4, being the wrist joint, providing +/−360° rotational motion of the quill. Robot grippers 55a,b are attached to the quill of each respective robot assembly 50a,b and are enabled to provide gripping action by pressure supplied from an air cylinder (not shown).

Referring now to FIG. 3(b), there is illustrated the precision conveyor 35 which is driven by drive motor assembly 42 at a rate sufficient to index and transfer approximately one oriented surgical needle per second (1 needle/sec) to the automatic swaging machine. A similar drive motor assembly 43 is provided for driving the indexing conveyors 25a,b. As will be explained in detail below, each drive motor assembly 42,43 is interfaced with and operate under the control of the control system 69 to pause the indexing motion to enable the pick-up and transfer of a needle from the indexing conveyor to the precision conveyor. In the preferred embodiment, the control system 69 includes a programmable logic controller (PLC) that is also in digital communication with the Adept® robot controllers and the vision tracking system components to control the infeed system.

As shown in FIG. 3(b), the vision tracking system comprises a camera assembly 60 having two video cameras 62 and 64, one located overhead each respective illuminated platform portion, 30a and 30b, for its indexing conveyor 25a. As will be explained in detail below, the video images of the needles obtained from each camera 62,64 are bit-mapped or suitably digitized and transmitted via suitable transmission media, such as communication lines 67a,b shown in FIG. 3(b), to the remotely located control system computer 69 where a Vision Control Task 160 processes the video images and inputs the data to each robot 50a,b via communication lines 197. Preferably, the conveyors 25a and 25b are translucent and are backlit at the respective portions 30a,b and 33a,b so that a sharp video image may be obtained by the overhead camera assembly for processing. It is understood that for descriptive purposes, only two video cameras 62,64 corresponding to the two illuminated platforms 30a, 30b are shown in FIG. 3(b). However, the invention includes a second set of video cameras (not shown) corresponding to illuminated platforms 33a and 33b for conveyor 25b so that, as mentioned above, binary images of needles on conveyor 25b may be obtained while the robots are picking and placing needles from conveyor 25a. The redundancy designed into this system ensures that there will be no momentary shortage of needles fed to the swaging station and that maximum throughput of oriented needles for input to the swaging station is achieved. In the event the state of robotics technology improves, and as the robot assemblies achieve greater degrees of movement at faster speeds, the second set of cameras and a second robot assembly may no longer be required. Furthermore, a robotic assembly of sufficient speed and precision may be able to pick up randomly deposited needles from a moving conveyor and place them directly in an oriented position at the swaging station.

In the preferred embodiment, each camera 62,64 is mounted approximately one (1) meter above each backlit indexing conveyor 25a,b and utilizes an electrically controlled telephoto lens with a focal distance ranging from 10 mm to 140 mm that may be changed with suitable adaptors. Suitable lens controllers are used to establish lighting/iris, focus, and field of view for each camera lens, and, are interfaced with the Adept® controller via an RS-232 link.

A further component of the control system for the needle sorting and infeed apparatus includes a SCADA Node (not shown) which is used to oversee and direct the infeed system. This node interfaces with each of the Adept® controllers via discrete RS-232 links which are used to download data information, such as needle parameters, error messages, and status messages, to the Adept® controllers during run-time. The SCADA node may comprise a personal computer or such suitable device, running commercially available FIXDMACS® software. Serial communication is used to exchange the needle parameters entered at the FIX/DMACS "Adept® Setup" screen during a needle changeover procedure to be described below. After an operator enters the needle parameters and initiates a changeover, the FIX/DMACS Node will transmit these parameters to the robot controller(s).

The robotic/vision control system 69 of the invention comprises individual computer software programs, each associated with a particular task to be performed by the needle sorting and infeed system 10 and executed under the control of the PLC 120. A flow diagram representation of the tasks to be performed and the PLC control signals for enabling such tasks is illustrated in FIGS. 8(a)–8(f). As shown in FIG. 7, the software for the robotic control system 69 of the instant invention performs eight (8) main tasks: a Robot Control task 150; a Vision Control task 160; a Conveyor Indexing Control task 180; a SCADA Node Interface task 195; A Control Panel task 260; a Task Manager 240; a Conveyor Initiation task 190; and, a Lens Control task 195. Of these eight tasks mentioned above, the first six are active during the needle infeed steady state operation as will be explained below. FIG. 7 additionally shows the data flow among the tasks and the signals which initiate the tasks. It is understood that the software language used in the preferred embodiment, is Adept's V/V+ language, which supports both vision and robotic control in a multitasking environment.

It should be understood to those skilled in the art that each robot assembly, controllers, and camera vision tracking system requires careful calibration and configuration procedures for the infeed system to properly function. For instance, each robot assembly requires that joint positions be set and joint limits be configured to ensure that the robots avoid structural damage when enabled. Furthermore, a camera-to-robot calibration is required so that the vision system may accurately compute the positional coordinates of the needle so that the robot may move to the pick position. This procedure provides a translation matrix between the camera's field-of-view and each robot base position.

The PLC 120 is responsible for initially powering the robot controllers and robots. A robot calibration procedure may be initiated after power-up to move the robot joints to known "home" positions to synchronize the digital encoders (not shown).

The process of starting the PLC 120, robot controllers, and conveyors 25a,b and 35 is time-critical. From the robot controller perspective, when a ROBOT ENABLE signal 219 is raised by PLC 120, it begins its normal cycle by executing the Robot Control Task 150, the Vision Control Task 160, the Conveyor Indexing Control Task 180, and the Conveyor Initiation Task 190; which initiates the movement of conveyor 25a, waits approximately up to two (2) seconds, and then initiates the movement of second conveyor 25b as will be described in detail below. The PLC simultaneously raises the ROBOT ENABLE signal on the other Adept robot. Under this scenario, the PLC integrates the startup of the Needle Infeed System, the Indexing Conveyors, and swaging machine with the raising of the ROBOT ENABLE signal 219. As will be explained in further detail below, when the ROBOT ENABLE signal goes low, the Adept robot halts its standard processing and responds to requests from the SCADA node.

Robot Control Task

There is a single Robot Control task associated with each Adept® controller for each robot assembly 50a,b although only one is indicated as element 150 in FIG. 7. The control system software for the Robot Control task 150 manages the respective robot assembly 50a or 50b as a resource, reads a FIFO buffer 155 of identified needle locations which are produced by and input from the Vision Control Task 160, interfaces with the programmable logic controller (PLC) 120 of control system 69 for needle placement handshaking, and, initiates the indexing of the conveyor belts 25a,b.

Figure 8A:
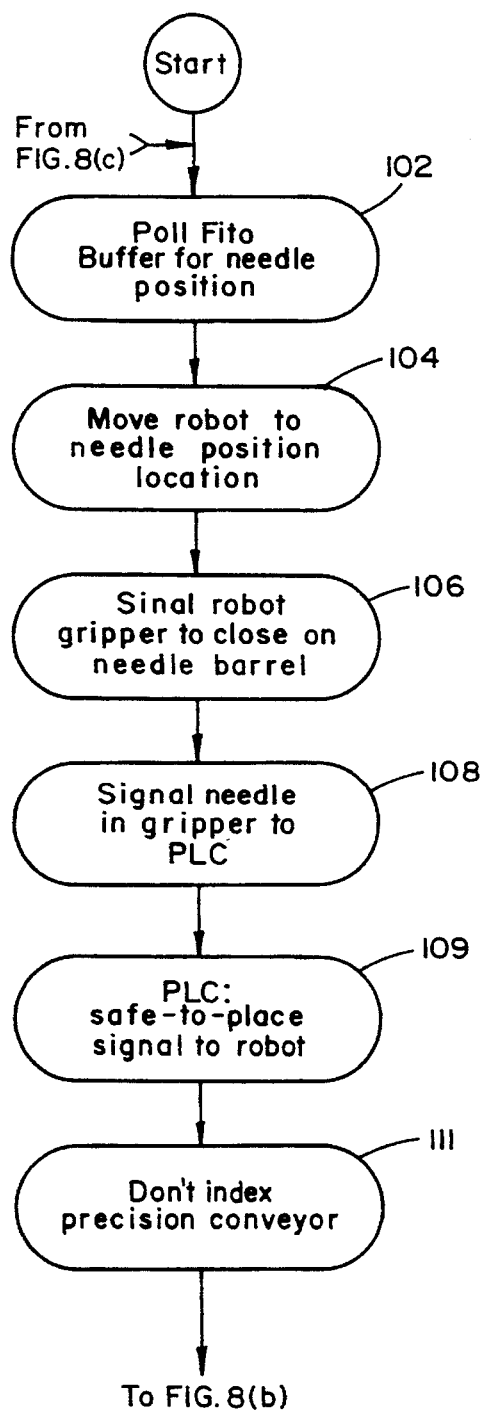
FIGS. 8(a)–8(f) illustrate the flow diagrams for the various robot control, vision control, and conveyor indexing tasks to be performed by the needle infeed control system of the instant invention.

As shown in the block diagram of FIGS. 8(a)–8(c), the steady state operation of the Robot Control task 150 for each robot assembly 50a, (50b) is as follows:

First, the respective robot controller continuously polls its input FIFO 155 via data line 193 to obtain positional coordinate data for the identified needle locations on a respective translucent conveyor 25a or 25b as indicated as step 102. The data for the needle locations are provided to the FIFO buffer from the Vision Control task 160 via respective data lines 197 as will be explained in further detail below. When an acceptable (recognizable) needle position is entered into the FIFO buffer 155, the robot controller will remove the needle position from the buffer and direct the robot gripper arm 55a,(55b) to move to that location on the conveyor belt as indicated at step 104. Next, for each recognized needle, the Robot Control task 150 will signal the robot gripper 55a,(55b) to close on the needle barrel portion 7 and to depart from the conveyor, as indicated at step 106, to an approach location proximate the precision conveyor 35. The robot control task then generates a NEEDLE IN GRIPPER signal 207 to the PLC as indicated at step 108 and waits for a response from the PLC 120. As shown as step 109 in FIG. 8(a), and, in further view of FIG. 7, when the PLC receives a Robot task generated NEEDLE IN GRIPPER signal 207, the PLC 120 will generate a SAFE TO PLACE signal 191 for receipt by each of the robots 50a,b. The purpose of the SAFE TO PLACE signal 191 is to inform the respective robot assembly 50a,b that a needle may be placed onto a precision conveyor boat 40 of conveyor 35. As a response to the receipt of the SAFE TO PLACE signal 191, the Robot Control task 150 will generate a DON'T INDEX PRECISION CONVEYOR signal 204 at step 111 for receipt by the PLC 120 immediately before it places the needle on the precision conveyor 35. While this signal remains high, for e.g., at a logic "1" state, the Adept® robot 50a or 50b will attempt to place a needle onto a boat 40 of precision conveyor 35 as indicated as step 113 in FIG. 8(b). This involves initiating the engagement jaws 47,49 of the precision conveyor engagement boat 40 to retract to allow the placement of the needle therebetween, as will be explained below. Once the movement of the robot has settled and a needle is placed, the Robot task 150 will generate a NEEDLE PLACE COMPLETE signal 206 for receipt by the PLC 120 at step 117, and, the PLC will generate a suitable control signal 209 to enable the engagement jaws of the precision conveyor engagement boat 40 to engage the needle at step 119. In the preferred embodiment, the dwell time of the NEEDLE PLACE COMPLETE signal 206 is approximately 48–64 milliseconds. After activating this signal, the robot assembly 50a,b will hold the needle in place for the same time period. (48–64 msec.) Immediately thereafter, the robot will open its grippers and move back to its approach location away from the engagement boat 40, as indicated as step 121 in FIG. 8(b). Finally, the DON'T INDEX PRECISION CONVEYOR signal 204 is removed at step 123 indicating that it is now clear for the PLC (and Conveyor Control task) to initiate the indexing of the precision conveyor 35 which is performed at the command of the PLC 120 at step 125 in FIG. 8(b).

Before indexing the As a safety interlock for conveyor index initiation, the Robot Control Task 150 will make a determination as to whether the current needle picked up is the last needle of the maximum number of (three) needles to be recognized in a camera's FOV and placed in the robot FIFO. This step is indicated as step 132 in FIG. 8(c). If the current needle picked is the last needle, the Robot task 150 for the current Adept will signal the Conveyor Indexing Control Task 180 with an internal control LAST PICK signal 192, 196 indicating that the respective robot assembly, 50a or 50b, has picked up the last needle from the current conveyor as indicated as step 134 in FIG. 8(c). If the maximum number of needles expected per camera field-of-view ("FOV") is not picked from the respective current infeed conveyor belt 25a(,b), e.g., only two needle locations were placed in the FIFO buffer as indicated at step 135 in FIG. 8(c), the Robot Control Task 150 will request the Conveyor Control task 180 to index that conveyor belt "early" via the INDEX CONVEYOR 1 EARLY or the INDEX CONVEYOR 2 EARLY signals 211,212, respectively, as shown in FIG. 7, and indicated as step 136 in FIG. 8(c).

Since all signals affecting the motion of the conveyors are routed through the Conveyor Control task 180, the Conveyor Control task will generate a corresponding INDEX CONVEYOR 1 EARLY, signal 211' or INDEX CONVEYOR 2 EARLY, signal 212', for receipt by the other Adept robot. If during normal operation a Robot Control Task receives either Index Conveyor 1 Early or the Index Conveyor 2 Early signal, it will flush the contents of its FIFO buffer 155 and continue as if the last needle has been picked from the conveyor.

As a result of receiving the INDEX CONVEYOR 1 EARLY, signal 211' or INDEX CONVEYOR 2 EARLY, signal 212' from the Conveyor Control task 180 indicating that the maximum number of needles have not been picked up or that there are no or insufficient needles in the respective camera's FOV, the other Adept robot will generate a corresponding CONVEYOR 1 INDEXED EARLY, signal 198', or CONVEYOR 2 INDEXED EARLY signal 199' for receipt by the Conveyor Control task 180, as shown in FIG. 7. These signals will cause the corresponding conveyor 25a(,b) to abort processing and initiate indexing of the belt.

The control software must take into account the floating 16–32 ms duration of a digital output based on the time slicing of V/V+. This will affect the calculation for minimum time required for placement in conjunction with setting and resetting the Don't Index Precision conveyor signal 204.

The Robot Control Task 150 performs error recovery on two type of errors. These errors are grouped as indexing errors and gross errors. As in all other tasks, gross errors cause the Task Manager 240 error recovery to respond and stop the Robot Control Task immediately. An indexing error occurs if a robot is waiting for a needle to be placed in its parts FIFO and both conveyor belts have not indexed within an appropriate amount of time. The Robot Control Task 150 recovers from this type of error by requesting the other robot to index early via INDEX CONVEYOR 1 EARLY (signal 211) or INDEX CONVEYOR 2 EARLY (signal 212). This forces both vision/robot control systems to flush the contents of its current parts FIFO and index the conveyor belts.

Conveyor Indexing Control Task

The Conveyor Indexing Control Task 180 initiates the indexing of each respective translucent indexing conveyor 25a,b and the task is initiated by the Conveyor Initiation task 190. All signals affecting the motion of the conveyors are routed through the Conveyor Control task 180, the flow diagram of which is illustrated in FIG. 8(d).

Figure 8B:
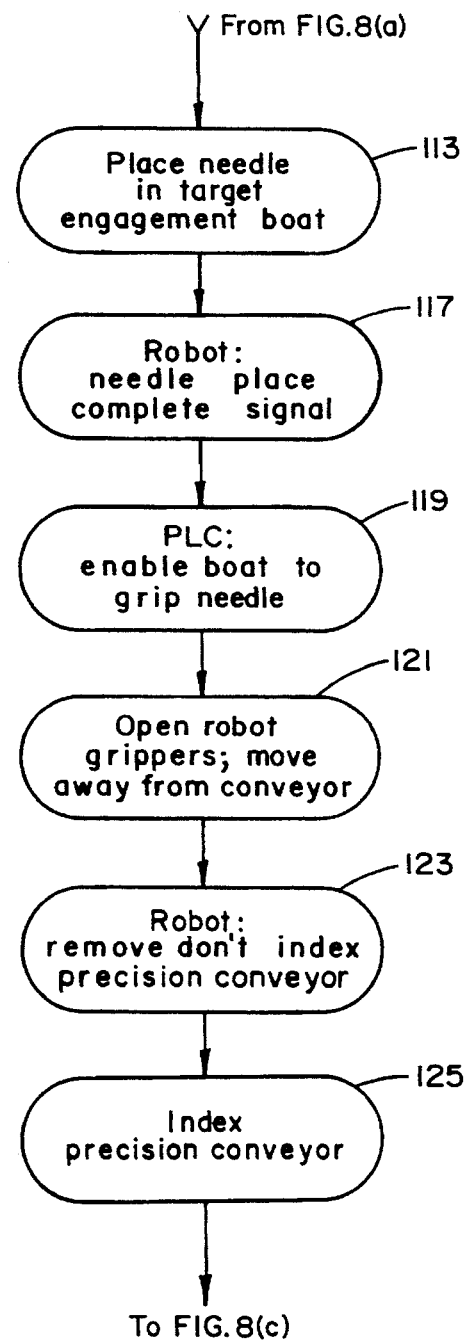
Figure 8C:
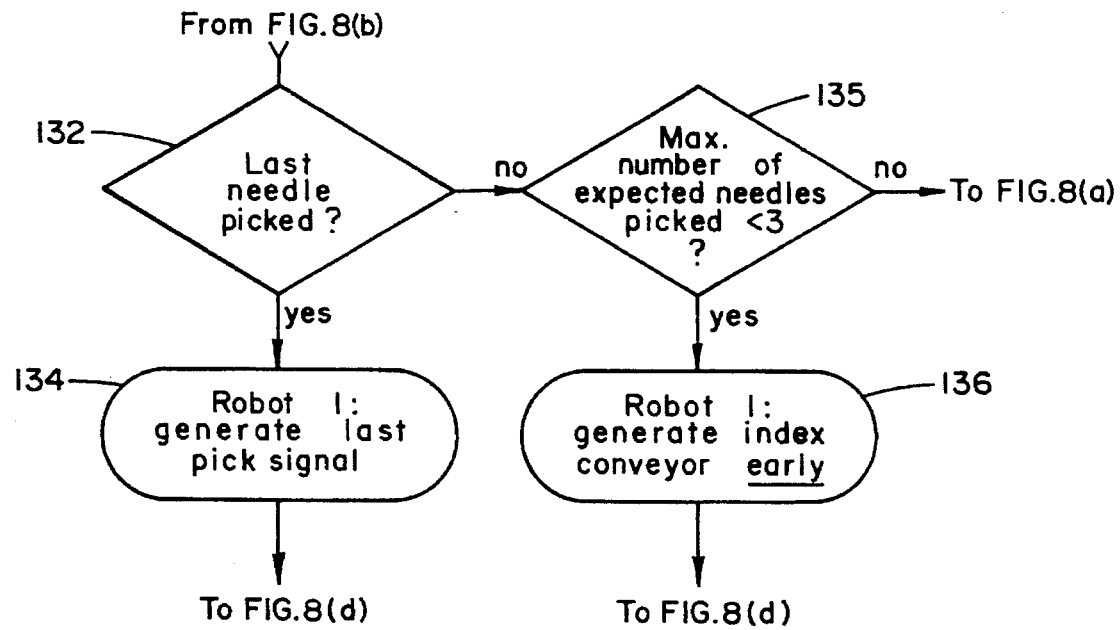
Figure 8E:
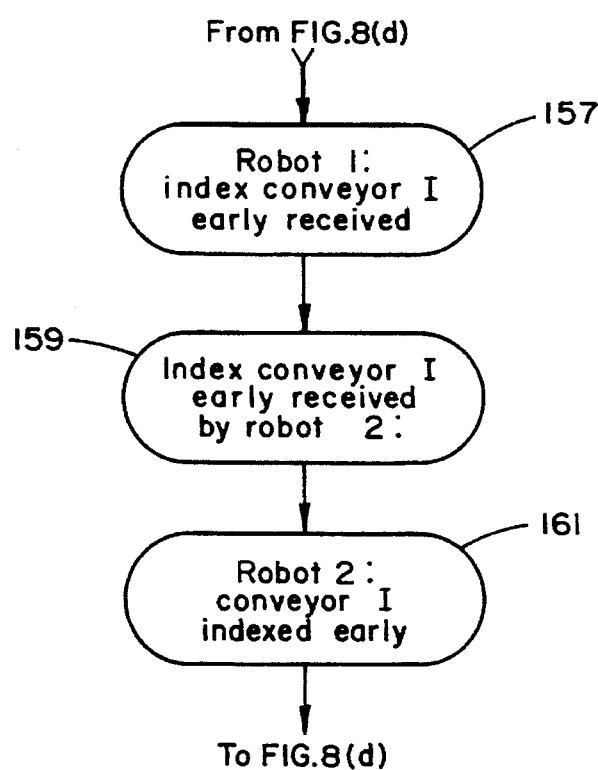
Figure 8D:
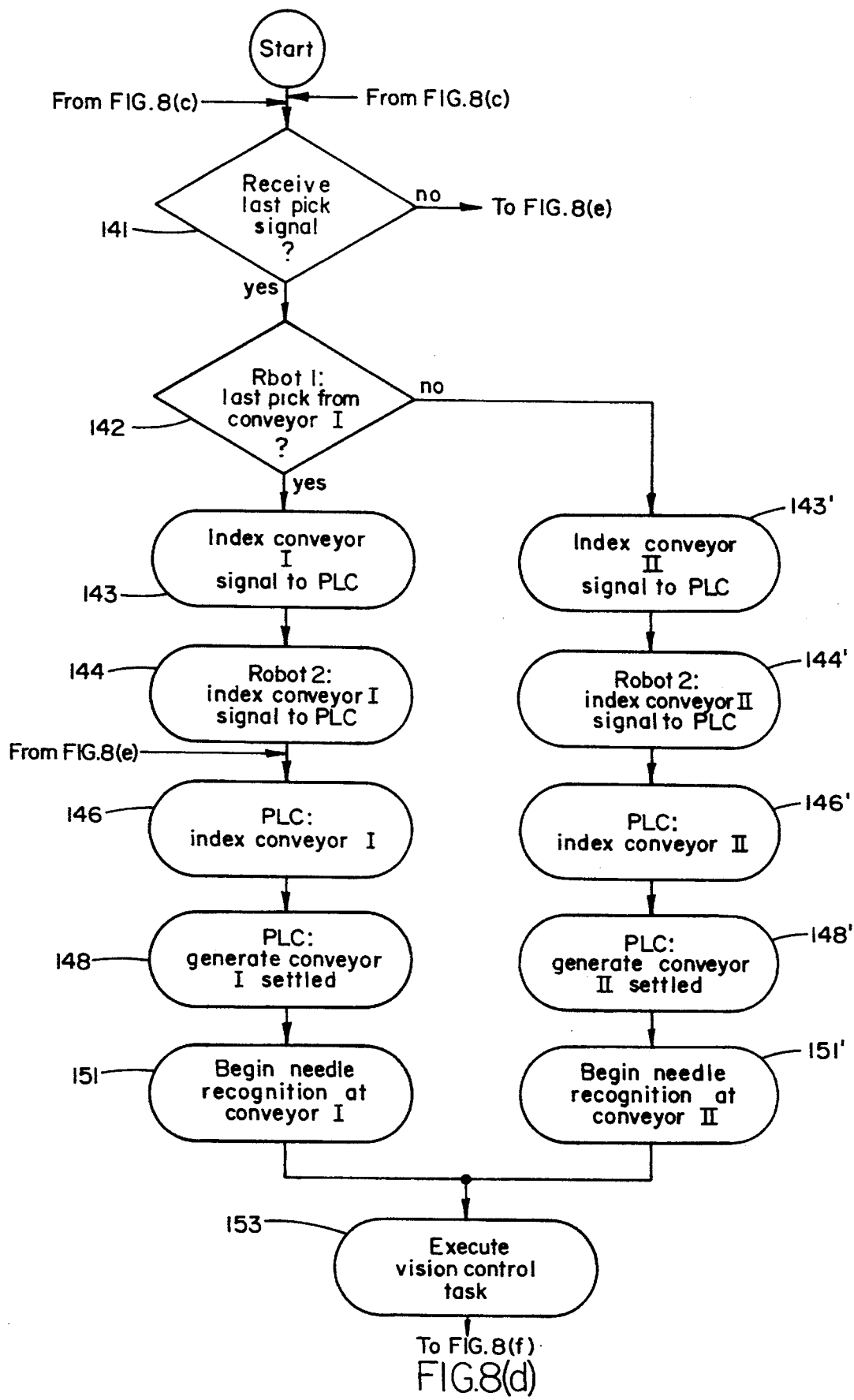

As shown in FIG. 8(d), and in further view of FIG. 7, the first step 141 of the Conveyor Indexing Control task 180 is to check for the LAST PICK signal 192,196 internally generated from the Robot Control Task 150 and indicating that the last needle pick-up from the respective infeed translucent conveyor 25a,25b has been completed by one of the Adept® robots 50a,b. For e.g., at step 142 in FIG. 8(d) the determination is made as to whether the Adept robot 50a (Robot I) has initiated the LAST PICK signal from Conveyor I (25a) or Conveyor II (25b). As a result of receiving the LAST PICK signals 192,196 from the robot task, the Conveyor Control task will generate a corresponding INDEX CONVEYOR 1 signal 198, or, an INDEX CONVEYOR 2 signal 199, for receipt by the PLC 120. This is indicated as respective steps 143 and 143' in FIG. 8(d). It is essential that each Adept® robot controller must request the PLC 120 to index a translucent indexing conveyor 25a(,b) after the last needle has been picked from the respective conveyor. Therefor, the other Adept® robot must generate its corresponding INDEX CONVEYOR 1 (or INDEX CONVEYOR 2) signal for receipt by the PLC at respective steps 144 and 144' before it can command the current translucent conveyor 25a,(25b) to index. Only after receipt of both INDEX CONVEYOR 1 (or INDEX CONVEYOR 2) signals 198,199 from each of the robot assemblies, as shown at steps 146 and 146', the PLC 120 commands the translucent indexing conveyor 25a to index, and, at steps 148 and 148', generates a corresponding CONVEYOR 1 SETTLED signal 241 or, a CONVEYOR 2 SETTLED signal 242 for receipt by the Conveyor Control Task 180. Note that the CONVEYOR 1 SETTLED signal 241 and the CONVEYOR 2 SETTLED signal 242 are raised approximately 2 seconds after the PLC has been requested by the robot control task 150 to index conveyor 25a, (25b). The Conveyor Control Task 180 then informs the Vision Control task 160 to begin needle imaging upon receipt of internal control signals 241',242' that correspond to the respective CONVEYOR 1 SETTLED or the CONVEYOR 2 SETTLED signals 241, 242. Once the indexing conveyor 25a (25b) has been indexed and the corresponding CONVEYOR SETTLED signal 241,242 has been received, the Vision Control Task 160 may begin needle recognition in the corresponding cameras's FOV, as indicated at step 151 and 151' in FIG. 8(d). Specifically, under the control of the Vision Control task 160, the cameras 62,64 of the recently indexed conveyor 25a(,b) will take a snapshot of the respective field of views at illuminated portions 30a,b thereof, and the task will process the image to make a determination of whether recognizable needles are present in each camera's field of view as indicated at step 153 in FIG. 8(d).

At this point, a distinction must be made between the mere presence or detection of a needle in the field of view and the presence of a "recognizable" needle. A needle may be present, but, for a variety of reasons, the Vision Task 160 may not be able to determine its positional coordinates until the camera vision parameters are changed by the execution of an auto-imaging algorithm which automatically adjusts the iris and vision system lighting parameters of each camera so that the cameras may subsequently obtain enhanced images that may be processed. During steady state, when the vision task has already "recognized" a needle in its respective field of view, the auto-imaging algorithm is not repeated. Details of the auto-imaging algorithm will be explained in detail below.

As an alternative to receiving the LAST PICK signals, the Conveyor Indexing Control task 180 may receive the INDEX CONVEYOR EARLY (1 and 2) signals 231,232 internally generated from the Vision Control task 160 when no needles are recognized in the current camera FOV, or, may receive the INDEX CONVEYOR EARLY (1 and 2) signals 211,212 internally generated from the Robot Control task 150 when the maximum number of needles are not picked. In either case, the Conveyor Control task 180 performs the following procedures as illustrated in the flow diagram of FIG. 8(e).

As indicated at step 157 in FIG. 8(e), the Conveyor Control task has received an INDEX CONVEYOR 1 EARLY signal, for e.g., signal 211 from Robot 1 of the Robot Control task 150 indicating that the maximum number of needles could not be picked from the Conveyor 1. The Conveyor Control task immediately generates a corresponding INDEX CONVEYOR 1 EARLY signal (211') for receipt by the Other Adept Robot as indicated at step 159. This signal informs the other Adept robot to stop processing Conveyor 1 needles and to index the belt. The other Adept robot will respond by generating a corresponding CONVEYOR 1 INDEXED EARLY signal (198') as indicated at step 161 in FIG. 8(e) to inform the Conveyor Control task 180 that the other Adept (e.g., Robot 2) will abort conveyor 1 processing and will index the conveyor 1 early as requested by the first Adept (Robot 1). Once these signals are received by Conveyor Control task, the task will immediately generate the INDEX CONVEYOR 1 signal (198) for receipt by the PLC which will initiate the early indexing of the requested conveyor belt, e.g. conveyor 1 (25a) as indicated in FIG. 8(d). The execution of the Vision Control task 160 will follow thereafter upon receipt of the CONVEYOR 1 SETTLED signal.

Vision Control Task

The Vision Control Task 160 controls and processes the images taken by each of the two camera assemblies 62,64. Since the timing of the two translucent conveyors are phased, only one camera is operating at one time.

Specifically, as shown in FIG. 3(b), the Vision Control task 160 interfaces with each camera 62,64 to identify the needle locations of recognizable needles in that camera lens's respective field of view encompassing an area located at respective illuminated platforms 30a,30b. The Vision Task 160 then processes the positional and orientation information of the identified needle locations and writes those locations to the Robot Task FIFO 155 via data lines 197. As mentioned above, the Vision Control task is additionally responsible for initiating an early conveyor index if no needles were imaged in a camera field of view.

As described briefly above, the Vision Control task runs each time either conveyor 25a,25b completes indexing. It is initiated to begin needle recognition upon receipt of either internally generated CONVEYOR 1 SETTLED signal 241' or CONVEYOR 2 SETTLED signal 242' which is generated by the PLC 120 and routed through the Conveyor Control task 180 each time respective translucent indexing conveyor 25a,25b has ceased indexing, as commanded by the Adepts. Each CONVEYOR SETTLED signal 241,242 goes high (logic "1") approximately two (2) seconds after the PLC has been requested by the Adept® robot to index a translucent indexing conveyor. Each of the CONVEYOR SETTLED signals 1 and 2 (241,242) remain high until the PLC 120 receives the next respective INDEX CONVEYOR 1 or 2 signal 198,199 from the Adept robots.

Figure 8F:
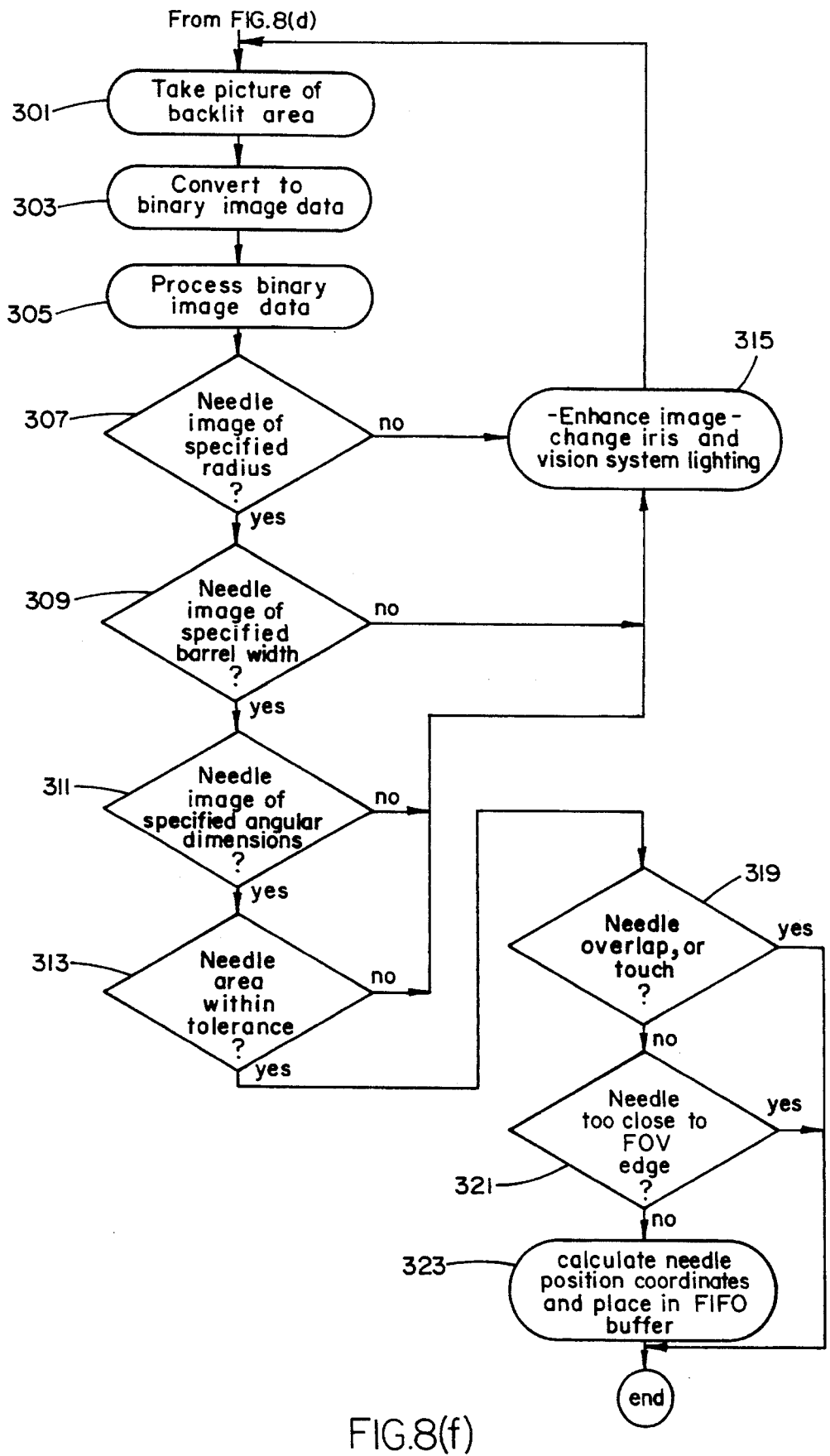

As illustrated in FIG. 8(f), the Vision Task 160 activates that camera which is associated with the conveyor settled signal. When activated, the camera 62,64 takes a picture of the backlit areas 30a,b of the conveyor belt 25a,(25b) as indicated at step 301. Any image obtained is preferably converted to binary image data as indicated at step 303 for subsequent digital processing, indicated at step 305. The Vision Control task 160 utilizes "vision tools" to detect acceptable needles, and places the coordinates of acceptable needle pick-up points in the FIFO buffer 155 for the Robot task. An "acceptable" needle in the backlit areas is a needle that measures within the tolerances of the needle parameters that have been previously accepted during the needle changeover procedure. The needle changeover procedure is a procedure to inform the infeed system software of the type and size of the needles in the current batch to be processed and must be executed before making needle batch changes as to be discussed below. Specified needle tolerances are for the needle radius, barrel width, angular characteristics of the needle with respect to the robots, and the calculated area as computed from the needle parameters.

Auto-Imaging Algorithm

As mentioned above, if a detected needle is unrecognizable, the auto-imaging algorithm is invoked to change the camera vision parameters. Thus, after the binary image data is processed at step 305 as shown in FIG. 8(f), a determination is made as to whether the needle image is of the specified radius (step 307), whether the needle image is of the specified barrel width (step 309), whether the needle image has the specified angular characteristics (step 311), and, whether the needle image area is within the specified tolerance (step 313). If any of these criteria are out of specification, then the auto-imaging algorithm is executed at step 315. The function of the auto-imaging procedure is to take a series of pictures of the same needle image at the respective camera's field of view to enhance the needle image for better needle recognition by improving the vision parameters between pictures. Thus, after each of the series of pictures is taken, the auto-imaging algorithm will automatically adjust the camera's iris and vision system lighting parameters to enable the vision system to image the needles properly within the camera's field of view. For example, when adjusting the lighting of the fields of view, certain camera vision parameters such as the gain, offset, and binary threshold may be modified. The auto-imaging algorithm is executed until a needle is recognized in each camera's field of view and is not repeated until a needle changeover is executed.

Even when the cameras of the Vision Control task 160 are adjusted, needle images may still not be imaged properly. This is because each camera's field of view utilizes a backlighting source and needles that overlap, touch with each other, or, are clipped by field of view edge boundaries will not be considered for recognition. Thus, as indicated in FIG. 8(f) at step 319, the Vision Control task will make a determination of whether the needles overlap or touch each other, and, at step 321, will determine whether the needles are too close to the edge of the field of view.

After all of the possible needles are recognized, the Vision Control task will calculate the needle pick-up coordinates of the acceptable needles and place them in the Robot Control task FIFO buffer 155 to enable the robot to pick and place the acceptable needle onto the precision conveyor, as indicated at step 323. In the preferred embodiment, the maximum number of needles that can be recognized during each dwell cycle of each translucent indexing conveyor is three (3). If less than this maximum or if no needles are recognized, a robot may be signalled to index the corresponding conveyor early, causing the vision system to abort its processing as described above.

Vision Task 160 is responsible for limiting the number of needle locations written to the FIFO to three, since the Robot Control Task will pick and place a needle for every needle location passed to the FIFO 155. In the preferred embodiment, the Vision Task is limited to operate for five seconds per indexing conveyor cycle.

The Vision Control Task 160 performs error recovery on three types of errors. These errors are grouped as imaging errors, processing errors, and gross errors. The gross errors cause the Task Manager error recovery to respond and stops the Vision Control Task 160 immediately. When an imaging error occurs, the Vision Control Task 160 suspends all execution on the current FOV and requests an early index of the conveyor belt by generating either INDEX CONVEYOR 1 EARLY or INDEX CONVEYOR 2 EARLY signals 231, 233 as discussed above. Receipt of these signals causes no needles to be placed in the parts FIFO and forces both vision/robot systems to pass on the current FOV of needles. If a processing error occurs, the Vision Control Task suspends all processing on the current needle and begins processing a new needle in the same FOV if another needle is available. As a result, the Vision Task does not insert the needle into the parts FIFO.

Conveyor Initiation Task

The Conveyor Initiation Task 190 functions to initiate the Conveyor Indexing Control task 180 and is started whenever the ROBOT ENABLE signal 219 is raised from the PLC 120. Once started, this task requests an INDEX INFEED CONVEYOR 1 (25a), signal 237, then waits approximately two (2) seconds, and requests an INDEX INFEED CONVEYOR 2 (25b), signal 239, as shown in FIG. 7. The task 190 is then terminated and is not restarted again until the ROBOT ENABLE signal 219 is lowered and raised again.

Task Manager

The Task Manager 240 initializes the software and hardware I/O signals, the global variables, and the vision/robot system tasks. Once the vision/robot system tasks are running, the task manager monitors the integrity and status of each task currently running and the resources that are controlled by these tasks. The status poll signals 247a–247f are indicated in FIG. 7. The resources are the robot, communication ports, and the I/O signal lines. The Task Manager reports any errors to the PLC, via the SYSTEM FAIL signal 222, and the SCADA node, via the SCADA Node Interface Task 195. The SYSTEM FAIL signal 222 is generated whenever a robot (as detected by the Task Manager) has recognized a gross error which prevents it from continuing operation. This signal is active-low and remains low until the Adept robot is reset. Thus, the PLC must lower the ROBOT ENABLE signal 219 immediately upon receiving this signal.

For gross errors occurring with the vision/robot control software, the Task Manager 240 is utilized to detect and recover from these errors by continuously polling the status and integrity of all steady-state tasks and resources during program execution. If it is determined that a gross error has occurred, the SYSTEM FAIL signal 222 will be raised to the PLC 120 and all tasks except the SCADA Node Interface Task, the Control Panel Task and the Task Manager will be stopped. A code indicating the reason for the last unrecoverable error will be available to the SCADA Node through the SCADA Node Interface Task. In some cases, an error message will be displayed in the Monitor Window of the Adept robot controller. After the SYSTEM FAIL signal is raised, the Task Manager will attempt to correct any problems detected on the robot and notify the operator through the Monitor Window. In most cases, the operator will only need to raise the ROBOT ENABLE signal again to re-set the vision/robot control software.

Control Panel Task

The Control Panel Task 260 presents a mouse controlled panel that allows an operator to access various software "debugging" utilities, to access diagnostics utilities, to control the speed of the robot, and to select new positions that the robot will move to for picking and placing needles. Also, the Control Panel Task allows the operator to stop the vision/robot system tasks from executing.

SCADA Node Interface Task

The SCADA Node Interface task 195 polls the SCADA Node RS-232 interface for messages from the SCADA node. The task will act as slave to SCADA Node requests for Adept and camera set-up procedures necessitated by product changeovers. These requests are valid only when the ROBOT ENABLE signal 219 is deactivated.

Lens Control Task

The Lens Control Task 270 is initiated only when the SCADA node requests a new product to be introduced to the vision system and is executed only as an off-line process. The Lens Control Task 270 accepts the new needle parameters and adjusts the field-of-view size for both cameras to accommodate the new product size. The zoom, focus, and iris lenses are affected by this new product introduction, as well as internal vision system parameters, such as gain, binary threshold, and offset, used for imaging. Once the cameras are adjusted, the task is suspended until another new product is introduced to the vision/robot system.

Product Changeover

Prior to enabling the robots to begin the needle infeed process, a Needle Changeover procedure is invoked to inform the Vision and Robot Control tasks of the control system software of the type and size of the needles to be processed. This needle changeover procedure must be completed before making needle batch changes. If a changeover is not completed before the first needle batch run after power-up, an error message will be displayed at the FIX/DMACS (SCADA Node) screen when the robots are enabled and the robots will not run. If a changeover is not completed between different needle batch runs, the vision tasks will not identify any needle being run.

Essentially, an operator of the system enters the needle parameters in appropriate units, e.g., millimeters and degrees at the FIX/DMACS screen of the SCADA task 195 through data lines 229. Such needle parameters for use by the Vision tasks include, the needle radius and the radius tolerance, acceptable needle angles and their tolerances, and, the needle width and the width tolerance.

In addition to inputting needle change parameters for the vision tasks, initial camera set-up parameters associated with the particular batch of needles to be processed are also input through the SCADA Node for use by the system. As shown in FIG. 7, the software utilizes the information provided by the user via the SCADA Node to automatically adjust the lens for the correct field-of-view size, focus, and zoom parameters prior to enabling the robots.

Figure 5A:
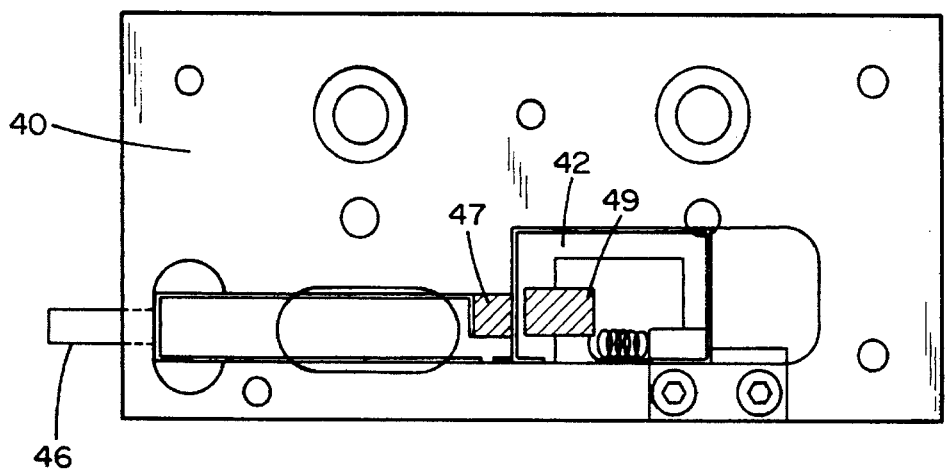
FIG. 5(a) is a detailed view of the precision conveyor boat having jaws for engaging and retaining an oriented needle for subsequent swaging.
Figure 5B:
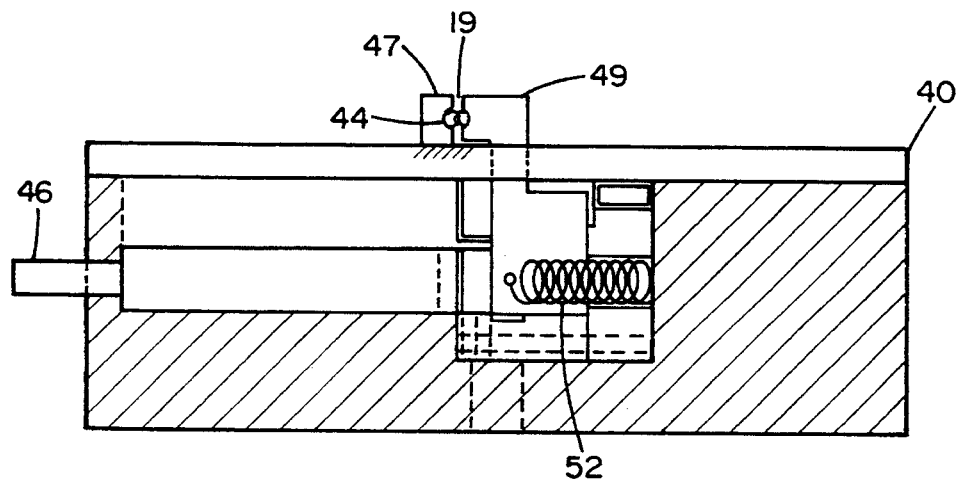
FIG. 5(b) is a detailed elevation view of the precision conveyor boat taken along line 5—5 of the boat illustrated in FIG. 5(a).
Figure 5C:
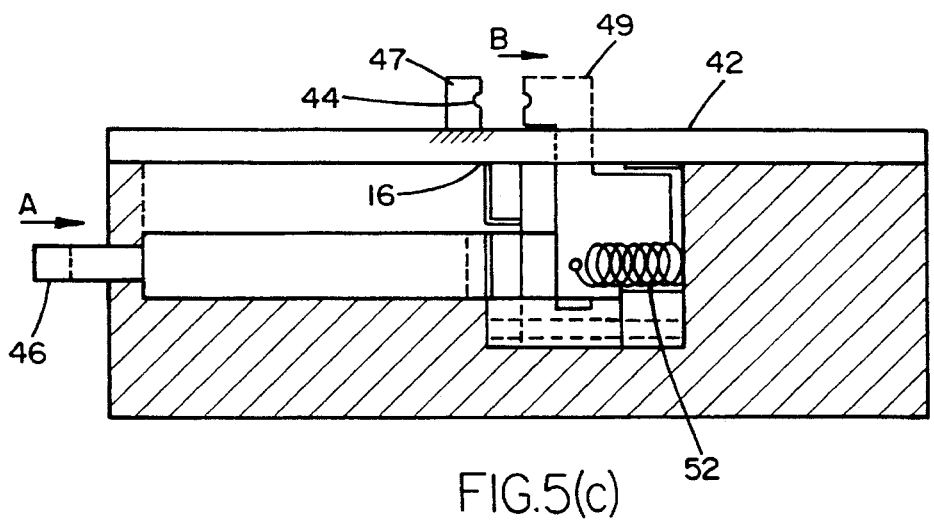
FIG. 5 (c) is a detailed view of the precision conveyor boat with movable jaw extended for placement of needle oriented for automatic swaging.

FIGS. 5(a)–5(c) illustrate the precision conveyor boat 40 to which each needle 19 is transferred by the robots. Each boat is preferably provided with a pair of jaws; one jaw 47 being fixedly mounted, and the second jaw 49 being slidable within pocket 42. In operation, a push rod 46 is pressed in the direction of the arrow "A" shown in FIG. 5(c) to compress spring 52 which retracts the position of the movable jaw 49 in the direction indicated by the arrow "B" to allow for placement of needle 19 within the notch 44 of both jaws. Normally, spring 52 is biased as shown in FIG. 5(b) to maintain movable jaw 49 in its engaged position for retaining a needle 19 in the notch 44. It should be understood that any type of releasable engaging mechanism may be provided for releasably retaining a needle 19 on conveyor boat 40, provided that each needle be correctly oriented on its respective boat for subsequent swaging to take place.

Figure 6:
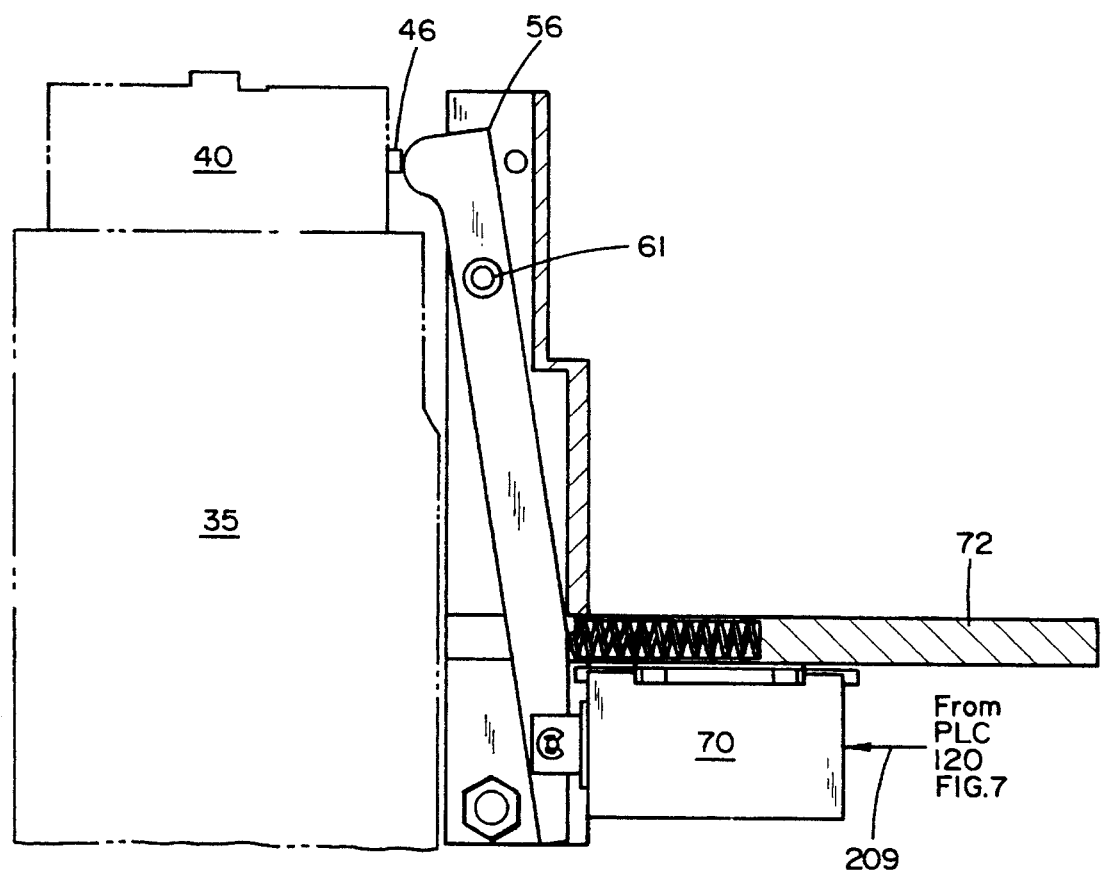
FIG. 6 is a side view of the robot load solenoid that actuates the jaws of the precision conveyor boat.

FIG. 6 illustrates a robot load solenoid mechanism 70 that is activated by the PLC 120 each time a needle 19 is being transferred to a precision conveyor boat 40 as described with respect to step 113 of FIG. 8(b). The robot load solenoid 70 may be mounted to the precision conveyor by an appropriate mounting plate 72. A sensor mounted on the precision conveyor, is also provided to sense the proximity of the precision conveyor boat 40. At such time a conveyor boat is dwelled for transference of a needle 19 thereto, a release arm 56 of the robot load solenoid is actuated by solenoid 70 at the initiation of the PLC 120 to pivot about pin 51 to depress push rod 46 and retract the movable jaw 49 to the position illustrated in FIG. 5(*c*). The robot gripper 55*a*,*b* then positions the needle 19 between the jaws 47,49 of conveyor boat 40 for engagement thereof. The release arm 56 is then retracted by spring 78 as the conveyor boat 40 resumes movement as initiated by the PLC 120 (See Step 113 FIG. 8(*b*)).

For automatic swaging to take place at the swaging station it is necessary that the needle be precisely positioned within the notch 44 of engagement jaws 47,49 of the boat 40. This is because the multi-axis gripper generally indicated at step 17 in the system flow chart of FIG. 1, must receive a precisely positioned needle for a suture (not shown) to be placed within the end 5 of needle 19. To ensure that each needle is uniformly oriented for transference to the multi-axis gripper of the automatic swaging station, a needle orientation device ("plow") 54 is provided as shown in FIGS. 9(*a*)–9(*e*) to orient each needle while engaged between jaws 47,49 on conveyor boat 40. The plow comprises an elongated arcuate blade 57 protruding from a mounting bracket 58 as best shown in FIGS. 9(*a*) and 9(*b*). In the preferred embodiment shown in FIG. 9(*c*), the plow is fixedly mounted at one end 48 of the precision conveyor 35 to enable arcuate blade 57 to scoop needle 19 positioned on the conveyor boat 40 while in forward motion. After contact is made, the arcuate portion 87 of the needle 19 is lifted and rolls over the arcuate blade 57 of the plow 54 as shown in FIGS. 9(*c*) through 9(*e*). Provision of the plow 54 ensures that each needle conveyed to the suture swaging station is oriented in the same direction.

Figure 10A:
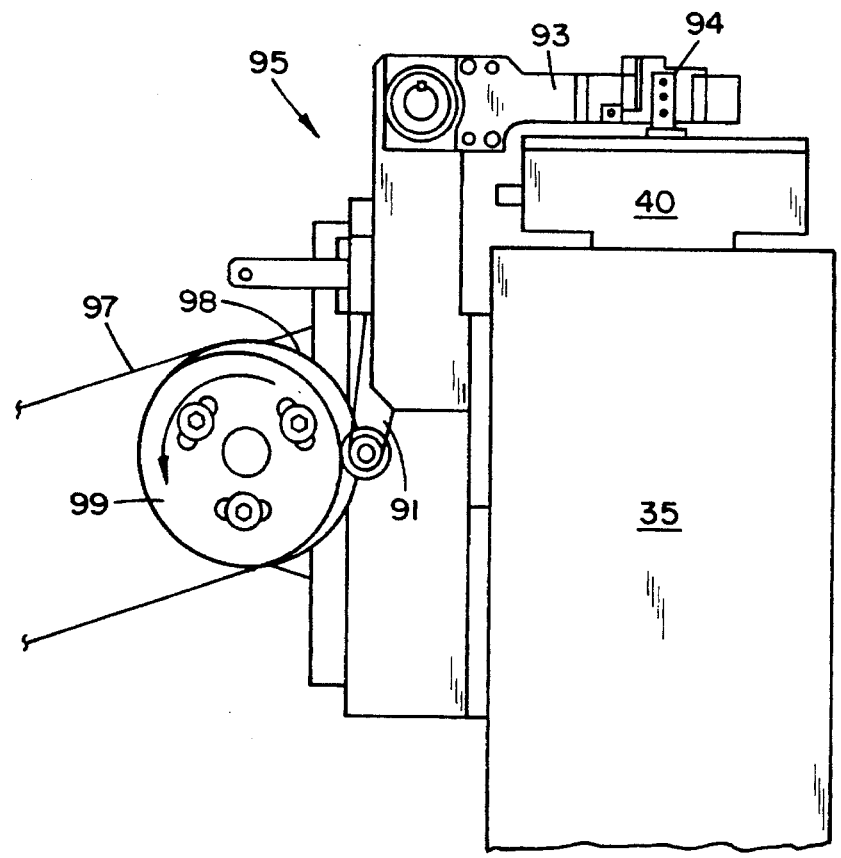
FIG. 10(a) is a side view of the needle hard stop assembly 95 for further orienting the needle 19 within the engagement jaws of conveyor boat 40.
Figure 10B:
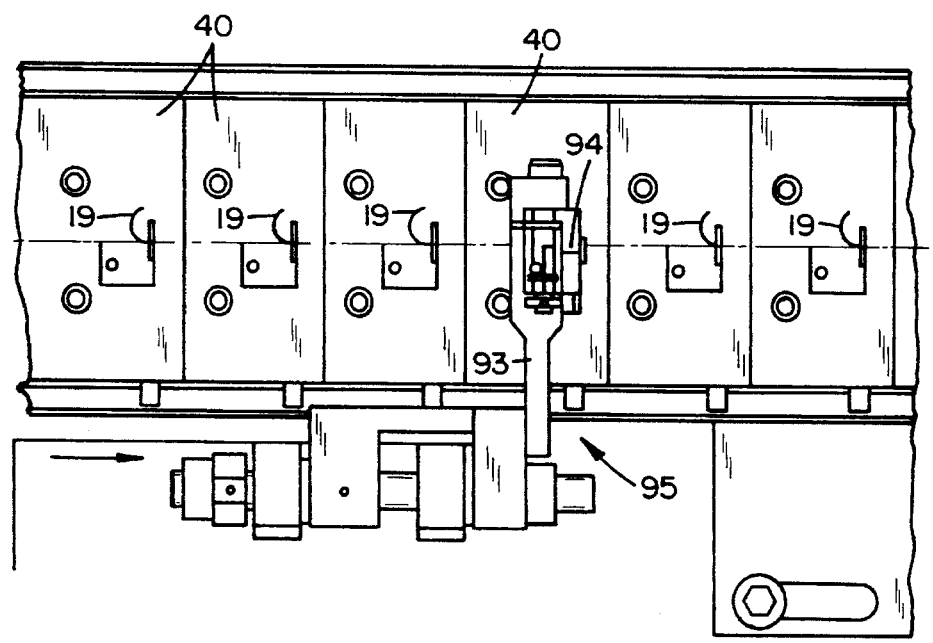
FIG. 10(b) is a top plan view of the needle hard stop assembly 95 for further orienting the needle 19 within the engagement jaws of conveyor boat 40.

Another mechanism is provided for further orienting the needle upon the precision conveyor boat is the needle hard stop assembly 95 illustrated in FIGS. 10(*a*) and 10(*b*). The hard stop assembly 95 comprises a pulley 99 operable by a drive motor (not shown) and timing belt 97 for rotating a cam 98 as shown in FIG. 10(*a*). Cam follower 91 is provided for actuating arm stop 93 to reciprocate from a first position above the engagement jaws 47,49 of conveyor boat 40, to a position that enables blade 94 of arm stop 93 to bear upon the end 5 of needle 19 while the precision conveyor boat 40 is conveyed in the forward direction as indicated by the arrow in FIG. 10(*b*). Impeding the forward motion of the needle 19 by blade 94 forces the needle to move within engagement jaws 47,49 of the conveyor boat 40 so that the engagement jaws 47,49 engage the needle at a precise location, for e.g., its barrel portion 83. Note that the cam 98, as driven by timing belt 97, is designed so that the arm stop 93 reciprocates in a timed relation with the forward motion of the boat 40 so that each needle upon each conveyor boat 40 is further oriented. After the needle is oriented, the arm stop 93 is reciprocated to its position above the conveyor boat 40 to await the next needle for further orientation in the manner heretofore described.

After the precision conveyor boat 40 is equipped with a properly oriented needle 19 in the manner described above, it is conveyed to an automatic swaging station (not shown) where a suture is fixedly attached to the needle. A stop assembly 80, shown in FIGS. 11(*a*) and 11(*b*), is the mechanism for executing a hard stop of the needle carrying conveyor boat 40 when the boat has reached the end of its destination at the needle swaging station. The blade 82 of the hard stop assembly 80 provides a fine tuning of the position of the needle upon the boat 40. Specifically, the blade 82 orients the needle to within 0.001 inches of the final position required for automatic swaging to take place.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. A control system for a needle infeed device for automatically transferring needles randomly positioned on a conveyor means to a precision engagement device at a further processing location, said needle infeed device comprising one or more robots each having a gripper means for picking and placing said needles, said control system comprising:

(a) control means for pausing said conveyor means to create a dwell cycle for said infeed device;

(b) at least one vision tracking means for each infeed device, each vision tracking means in communication with said control means for creating an image of said needles during each dwell cycle at one or more predetermined locations on said conveyor means and for calculating positional and orientation data for each needle from the image obtained at said predetermined location during said dwell cycle;

(c) memory means for temporarily storing said positional and orientation data received from said vision tracking means; and (d) robot control means for accessing said stored positional and orientation data to select one of said imaged needles, the positional and orientation data stored in said memory means, and enabling said one of said robots to pick up one of said imaged needles in accordance with its respective positional and orientation data and to place said needle in said precision engagement device.

2. The control system for a needle infeed device as claimed in claim 1 wherein said needle infeed device includes a drive means for driving said conveyor means, said robot control means generating a first signal for receipt by said control means requesting said control means to enable said drive means to index said conveyor means.

3. The control system for a needle infeed device as claimed in claim 2 wherein said control means generates a first signal for receipt by said vision tracking means indicating that said conveyor means has finished indexing and is in said dwell cycle.

4. The control system for a needle infeed device as claimed in claim 2 wherein said robot control means automatically polls said memory means to obtain current positional and orientation data of each recognized needle for said robots, said robot control means generating said first signal for receipt by said control means to further index said conveyor means when no positional and orientation data is available in said memory means at a current dwell cycle.

5. The control system for a needle infeed device as claimed in claim 1 wherein said vision tracking means includes one or more camera means for obtaining a video image of said needles on said conveyor means at each of respective said one or more predetermined locations within a field-of-view of each of said one or more cameras.

6. The control system for a needle infeed device as claimed in claim 5 wherein each of said cameras has a plurality of vision parameters associated therewith, said vision tracking means including means for comparing needle parameters obtained from said video image with one or more acceptable needle parameters associated with a current batch of needles to be processed, said one or more needle parameters selected from the group including needle radius, needle angle, and needle width.

7. The control system for a needle infeed device as claimed in claim 1 wherein said vision tracking means further includes means for automatically enhancing said image of a needle by recording successive images of said needle and adjusting one or more of a plurality of vision parameters between each successive image until said image of said needle is acceptable for obtaining positional coordinate data therefrom.

8. The control system for a needle infeed device as claimed in claim 7 wherein said vision parameters include field of view size, iris control for said camera and vision system lighting control for said camera.

9. The control system for a needle infeed device as claimed in claim 1 wherein said positional and orientation data includes positional coordinates of each recognized needle for said robots, said control means enabling said gripper means of each said one or more robots to pick up said one or more needles at said positional coordinates, said robot control means further generating a second signal for receipt by said control means indicating said one or more needles have been picked up by said robot gripper means.

10. The control system for a needle infeed device as claimed in claim 9 wherein said engagement device is located on a second conveyor means having a drive means associated therewith for indexing said needle to said processing location, said robot control means generating a third signal for receipt by said control means requesting said control means to pause said indexing of said second conveyor means to create a second dwell time therefor.

11. The control system for a needle infeed device as claimed in claim 10 wherein said control means generates a signal for receipt by said robot control means indicating that said robot gripper means may place said needle in said engagement device during said second dwell time.

12. The control system for a needle infeed device as claimed in claim 11 wherein said robot control means generates a fourth signal for receipt by said control means indicating that said one or more robots have placed said needles in said engagement devices, said control means enabling first and second jaws of said engagement device to grip said needles placed therein.

13. A method for controlling an automatic infeed device for feeding surgical needles from one location to another location, said infeed device having a first conveyor having randomly positioned needles located thereon, a second conveyance having a plurality of precision needle engagement devices located thereon, and one or more robot means each having a gripper means for picking up a needle from said indexing conveyor, said method comprising the steps of:

(a) pausing said first conveyor to create a dwell time for said infeed device;

(b) imaging said needles on said conveyor with a vision tracking means during said dwell time to create an image of said needles;

(c) calculating positional and orientation data from said image of said needles and determining acceptable needle locations for said one or more robot means to select a needle for each of said robot means;

(d) picking up said selected needle at said acceptable needle location with said one or more robot gripper means; and, (e) placing each needle in said precision engagement devices for subsequent conveyance thereof.

14. The method for controlling an automatic infeed device for feeding surgical needles from one location to another location according to claim 13, wherein said step (a) of pausing said first conveyor further includes the step of generating a first control signal from said robot means requesting a control means for said first conveyor to inhibit motion thereof during said dwell time.

15. A method for controlling an automatic infeed device for feeding surgical needles from one location to another location according to claim 14 further including the step of generating a second control signal from said robot means for said control means requesting said control means to index said first conveyor means when no acceptable needle locations are available.

16. The method for controlling an automatic infeed device for feeding surgical needles from one location to another location according to claim 13, wherein said step (b) of visually tracking said needles on said conveyor during said dwell time to determine acceptable needle locations for said one or more robot means further includes the steps of:

(a) generating a signal for said vision tracking means indicating that said first conveyor means is in said dwell cycle;

(b) obtaining an image of said needles from one or more camera means each having a field of view at one or more predetermined locations on said conveyor means;

(c) processing said image to determine positional coordinates for recognizable needles present in said image; and, (d) inputting said positional coordinates into a memory means for access by said robot means.

17. The method for controlling an automatic infeed device for feeding surgical needles from one location to another location according to claim 16, wherein said processing step (b) further includes the steps of:

(a) determining one or more needle parameter values for needles identified in said image, said one or more needle parameters selected from the group including needle radius, needle angle, and needle width; and (b) comparing each of said needle parameters values obtained from said image with a predetermined range of acceptable needle parameter values associated with a current batch of needles being processed.

18. The method for controlling an automatic infeed device for feeding surgical needles from one location to another location according to claim 16, wherein said processing step (b) further includes the step of determining whether needles located in said field-of-view overlap with each other.

19. The method for controlling an automatic infeed device for feeding surgical needles from one location to another location according to claim 13, which further includes an image enhancing step to calibrate the device, the enhancing step including the steps of:

(a) successively obtaining a series of images of one of said needles during said tracking step; and (b) adjusting one or more of a plurality of camera vision parameters selected from the group including field of view size, iris control for said camera, and vision system lighting control for said camera, between each successive image until said image of said needle is acceptable to obtain data to determine acceptable needle locations.

20. The method for controlling an automatic infeed device for feeding surgical needles from one location to another location according to claim 13, wherein said step (*d*) of placing each said needles in an engagement device further includes the steps of:

(a) pausing said second conveyance having said needle engagement devices located thereon to create a second dwell time for said infeed system; and, (b) generating a control signal indicating to said one or more robot gripper means to place a gripped needle in said needle engagement device during said second dwell time.

21. The method for controlling an automatic infeed device for feeding surgical needles from one location to another location according to claim 20, said method further including the step of generating a signal for enabling a pair of jaws of said engagement device to grip said needle after placement therein by said robot gripper means.

22. The method for controlling an automatic infeed device for feeding surgical needles from one location to another location according to claim 20 further including the step of actuating a push rod means for retracting one jaw of said pair of engagement jaws for enabling the positioning of said needle therebetween, said actuating step occurring prior to the placement of said needle between said pair of engagement jaws.

23. The method for controlling an automatic infeed device for feeding surgical needles from one location to another location according to claim 20 further including the step of orienting said needle while positioned upon said second conveyor means.

* * * * *